United States Patent [19]

Balmat

[11] 3,998,622

[45] Dec. 21, 1976

[54] RHODIUM FROM HYDROFORMYLATION STILL HEELS

[75] Inventor: Jean Louis Balmat, Kennett Square, Pa.

[73] Assignee: E. I. Du Pont de Nemours and Company, Wilmington, Del.

[22] Filed: Dec. 23, 1975

[21] Appl. No.: 643,913

[52] U.S. Cl. .............................. 75/.5 AB; 75/.5 A
[51] Int. Cl.² ..................... B22F 9/00; C22B 34/00
[58] Field of Search ....................... 75/.5 AB, .5 A

[56] References Cited
FOREIGN PATENTS OR APPLICATIONS
1,185,332  3/1970  United Kingdom ............... 75/.5 A

*Primary Examiner*—Arthur J. Steiner

[57] ABSTRACT

A process for preparing a high surface area zero valent rhodium in the form of small, hollow, porous agglomerates of rhodium particles by adjusting the pH of still heels from the hydroformylation reaction of unsaturated hydrocarbons with a base until a pH of from about 3 to 8 is attained, heating the still heel in the presence of water to a temperature of about 115° to 175° C until the rhodium separates, the ratio of water to still heel being from about 0.1:1 to 1:1 and recovering the rhodium in the form of small, hollow, porous agglomerates of rhodium particles.

11 Claims, 5 Drawing Figures

RHODIUM FROM HYDROFORMYLATION STILL HEELS

BACKGROUND OF THE INVENTION

1. Field of the Invention

This invention relates to a novel form of rhodium metal and to a process for the preparation of said rhodium metal. More specifically, this invention relates to rhodium metal in the form of small, porous, hollow agglomerates of rhodium particles and a process for the preparation of said rhodium from rhodium containing still heels.

2. Prior Art

Rhodium metal is known in the art. It is available commercially and is known to be useful in hydroformylation reactions as a catalyst. In such reactions the rhodium may be complexed with various ligands to render it catalytically active. Normally available rhodium metal, however, does not readily react with ligands to form the liquid complex referred to above. There is a need for a rhodium metal form that can be more readily solubilized to the rhodium complex required for hydroformylation reactions.

SUMMARY OF THE INVENTION

Now rhodium metal has been discovered in a unique form that permits its more ready conversion to a liquid hydroformylation catalyst complex.

Figure 1:
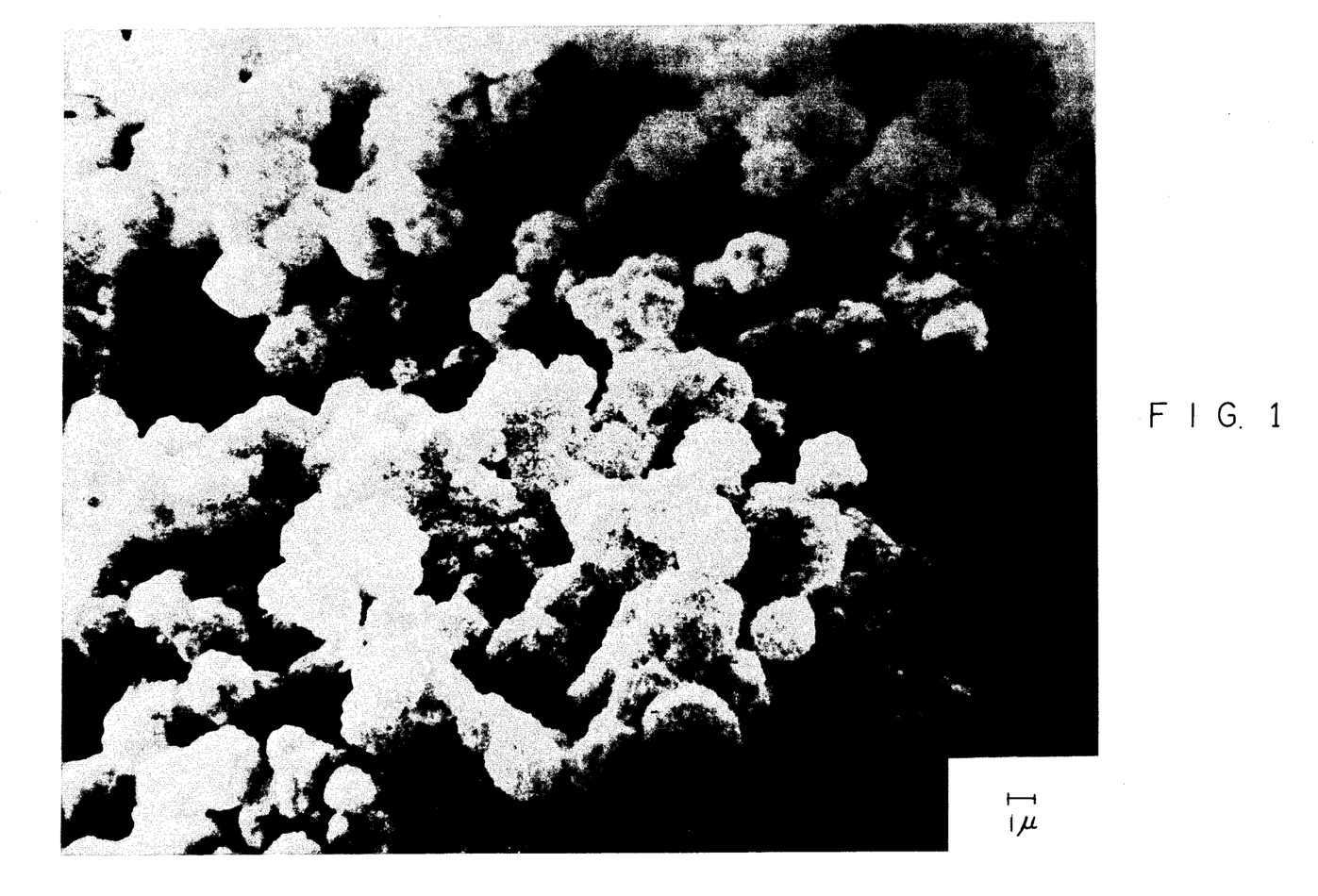
FIG. 1 is an electron microscope photograph at 6,000 magnification of rhodium of the present invention.
Figure 2:
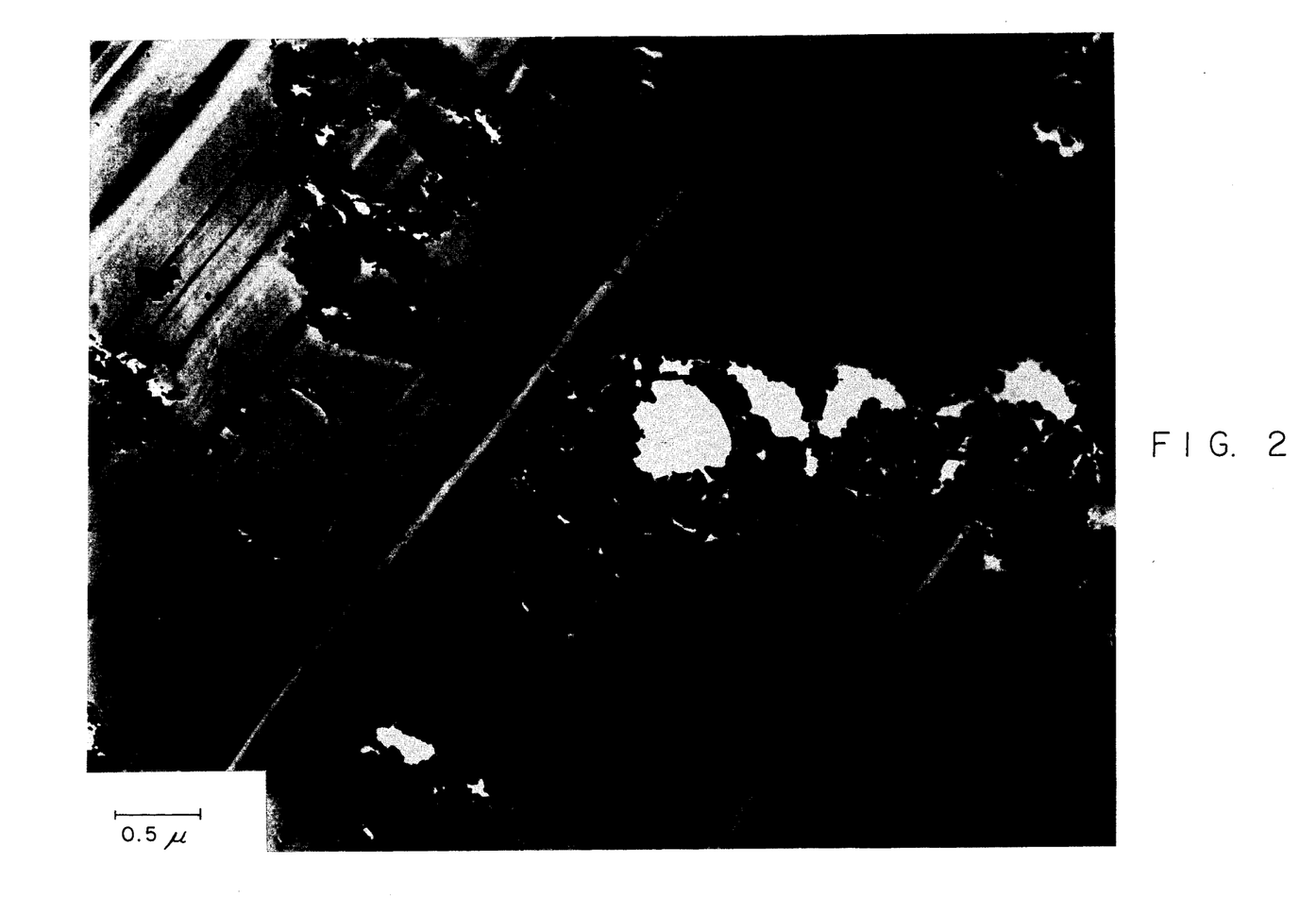
FIG. 2 is an electron microscope photograph at 40,000 magnification of rhodium of the present invention. The rhodium was incorporated in plastic and microtoned slices were used to obtain the photograph designated FIG. 2.

Thus in accordance with the invention, I have found rhodium in the form of small, porous, hollow agglomerates of particles of zero valent metallic rhodium. This new rhodium metal has a relatively high surface area as is apparent from the particle size in the electron microscope FIGS. 1, 2 and 3. Purities of the rhodium obtained by the present invention have been as high as 80%.

A comparison of the figures clearly indicates the difference in form between the hollow, porous agglomerates of solid rhodium particles of the present invention and the irregular shaped solid particles of comerical rhodium.

The rhodium of the present invention is prepared by a process comprising adjusting the pH of still heels to from about 3 to 8 with a base, heating the still heels to from about 115° to about 175° C in the presence of water for a time sufficient to separate the rhodium from the ligand of the rhodium complex and recovering metallic rhodium in the form of small, porous, hollow agglomerates of particles.

The still heels referred to herein are heels or tails remaining after the distillation of the reaction product from the hydroformylation of unsaturated hydrocarbons, e.g., olefinic cyclic acetals conducted in the presence of a rhodium trialkyl phosphite ligand complex catalyst. The reaction product which includes, e.g., cyclic acetal aldehydes is distilled to remove the cyclic acetal aldehyde product, unreacted cyclic acetals and excess ligand. The residue tails or heels from said distillation are referred to herein as still heels. Such still heels contain a variety of compounds which include high boiling compounds and rhodium complex catalyst. By rhodium complex catalyst is meant a coordination compound of rhodium in complex combination with carbon monoxide, hydrogen and a trialkyl phosphite ligand. Generally the pH of still heels are acidic. The pH may range from 1 to about 8.

Hydroformylation reactions, from which the still heels of the present invention are derived, are reactions of unsaturated hydrocarbons, e.g., olefinic cyclic acetals with hydrogen and carbon monoxide in the presence of a rhodium catalyst at temperatures and pressures well known in the art. Rhodium complex catalysts used are solubilized complexes of rhodium in combination with carbon monoxide, hydrogen and trialkyl phosphite ligand. After the reaction products from the hydroformylation of the unsaturated hydrocarbon are distilled to recover the desired product and excess ligand, the residue of high boilers and rhodium catalyst complex is usually recycled back to the hydroformylation reaction until high boilers accumulate to the point where a small portion of the still heels must be purged to maintain the high boilers at a constant concentration. The value of rhodium is such that economics do not permit the discarding of all or any significant portion of the residue. The process of the present invention permits the recovery of rhodium metal in a novel and unique form which is more active than commercially available rhodium metal.

The base for adjusting the pH of the still heels of the present invention may be any base material that is soluble in the still heel water mixture of the present invention and will not form any interfering precipitation. The base may be weak or strong. For example, sodium hydroxide or salts of weak acids and strong bases can be used. From the standpoint of availability, the preferred base is selected from the group consisting of alkali metal hydroxide and alkaline earth metal hydroxides. The most preferred base is the alkali metal hydroxides among which sodium or potassium hydroxide are most preferred.

The amount of base required will vary depending on the particular still heel utilized. Generally the amount of base required will be that amount that will give the still heel a pH of from about 3 to 8. An excess of base will reduce the percent of the rhodium recovered from the rhodium available in the still heel. Depending on the nature of the still heel the pH may be such that no base need be added. It was noted that as the amount of free base present in the still heels after the treatment according to the present process increased the recovery of rhodium decreased. Generally the pH of the still heel after treatment according to the process of the present invention may range from about 3 to 7.

After the pH of the still heel has been adjusted, the still heels is heated in the presence of water to a temperature of from about 115° to about 175° C, preferably 130° to 160° C, for a time sufficient to separate the rhodium, that is present in the still heel in the form of a complex with a ligand, from the ligand. Generally the higher the temperature, the greater the recovery. Generally the time at the temperatures indicated can vary from about 15 minutes to 120 minutes. At shorter periods of time, the yield of rhodium recovered is lower. Longer periods are operable but offer no advantage.

The thermal treatment of the still heels after pH adjustment must be done in the presence of water. However, the thermal treatment of this invention may be accomplished in the presence of water and alcohol or water and an organic liquid. By alcohol is meant any alcohol soluble in the still heel of the present invention. Many generally available alcohols may be used in the process of the present invention, but for reasons of cost methanol, ethanol, propanol, butanol and mixtures thereof are preferred. By water and alcohol or water and an organic liquid is meant mixtures of water with alcohols, alcohols containing water therein and aqueous waste streams containing mixtures of water with organic liquids. Organic liquids may include alcohols, aldehydes and ketones. The alcohol or organic liquid merely serves to decrease the viscosity of the still heel mixtures to facilitate filtration of the rhodium. Thus, the alcohol and the organic liquid are optional.

The amount of water or water and alcohol or water and organic liquid mixture required in the process of the present invention may vary widely. Generally the ratio of water or water/alcohol or water/organic liquid mixture to still heel is such that the weight ratio of water to still heel is from 0.1:1 to 1:1. An amount of water less than 0.1 part per part of still heel results in lower rhodium recovery while an amount significantly greater than 1 part per part of still heel results in the preparation of rhodium made up of particles so small they cannot be easily recovered by filtration or centrifugation.

Representative examples of alcohol of the present invention include methanol, ethanol, propanol, butanol, ethylene glycol, propylene glycol and mixtures thereof.

After the thermal treatment of the still heels, the rhodium separated from the ligand and in metallic form is recovered by filtration or centrifugation.

According to the process of the present invention the rhodium recovery from the still heels is at least 90% of the rhodium present in the still heels. Accordingly, the process of the present invention is a process for the recovery of at least 90% of the rhodium present in still heels, said process comprising
 a. adjusting the pH of the still heels from about 3 to 8 with a base selected from an alkali metal hydroxide and an alkaline earth metal hydroxide;
 b. heating the solution from (a) for from about 15 minutes to about 120 minutes at about 115° to about 175° C in the presence of water or a mixture of water and alcohol, the ratio of water to still heel being from about 0.1:1 to 1:1; and
 c. recovering metallic rhodium in the form of porous, hollow agglomerates of particles.

The rhodium complex catalyst of the present invention that is present in still heels is a homogenous catalyst solution comprising rhodium and biphyllic ligands complexed with carbon monoxide and hydrogen through coordinate bonding. The biphyllic ligands are tertiary organo phosphorous compounds of the formula wherein $R_1$, $R_2$ and $R_3$ are the same or different alkyl groups having 1 to 12 carbon atoms. Representative examples of such alkyl groups include methyl, ethyl, propyl, octyl, pentyl, decyl, dodecyl and mixed esters of methyl, ethyl or isopropyl. Representative examples of the ligand include trimethyl phosphite, triethyl phosphite, tri-n-propyl phosphite, triisopropyl phosphite, tri-n-hexyl phosphite, triisooctyl phosphite, dimethyldodecyl phosphite, tridecyl phosphite, methyl ethyl propyl phosphite and other combinations within the scope of the above formula. The lower boiling phosphite ligands wherein $R_1$, $R_2$ and $R_3$ are methyl, ethyl, n-propyl and isopropyl are more conveniently applied to the present invention.

The phosphite ligand forms a complex with rhodium and carbon monoxide as described in U.S. Pat. No. 3,527,809 and the complex catalyzes the hydroformylation reactions from which the still heels of the present invention are derived. An excess of the phosphite over that which is required to complex the rhodium must be used in order to favor linear vs branched hydroformylation. The excess ligand is also necessary to insre the stability of the rhodium catalyst throughout the hydroformylation reaction.

Commercially available $Rh_6(CO)_{16}$ is charged into a pressure vessel with an olefinic starting material, e.g., 2-vinyl-5-methyl 1,3-dioxane, solvent and ligand. After flushing with nitrogen, the pressure vessel is sealed and pressurized with carbon monoxide and hydrogen to 35 to 150 psig at a hydrogen to carbon monoxide ratio of 1:1 and after a period of time the reaction is complete. The product consists of various aldehydes, unreacted starting material, cyclic acetals, ligand, rhodium complex catalyst and high boilers. This is subjected to distillation having a residue made up of rhodium complex catalyst and high boilers (HB). Rhodium, recovered by the process of the present invention from this residue of HB and rhodium complex catalyst was added to trimethyl phosphite, carbon monoxide and hydrogen at a 1:1 ratio and a pressure of 4,000 psig and it was determined that in a two hour period 95% of the rhodium of the present invention was solubilized or converted to a homogenous complex solution at 150° to 175° C. Repeating the same procedure except that commercially available rhodium was added to trimethyl phosphite, carbon monoxide and hydrogen at a 1:1 ratio and a pressure of 4,000 psig 14% of the commerical rhodium was solubilized or converted to a homogenous complex solution in the same time period.

The form of the rhodium of the present invention is believed to be the reason for the above advantages over commercial rhodium. The zero valent or metallic rhodium of the present invention consists of small, hollow porous agglomerates of particles having a surface area about five orders of magnitude greater than an equivalent weight of commercial rhodium. The individual particle sizes of the rhodium of the invention generally range rather widely from an average particle size of from about 0.01 to 0.5 micron in diameter with a density of about 12.4 g/cm³. The porosity is clearly visible under the electron microscope in FIGS. 2 and 3. The porous hollow agglomerates of particles generally may have a diameter of from about 0.5 to 6 microns, with walls of about 0.1 to 1.0 micron. The surface area of the rhodium of this invention may vary somewhat but generally is about 1 square meter per gram or more.

Figure 3:
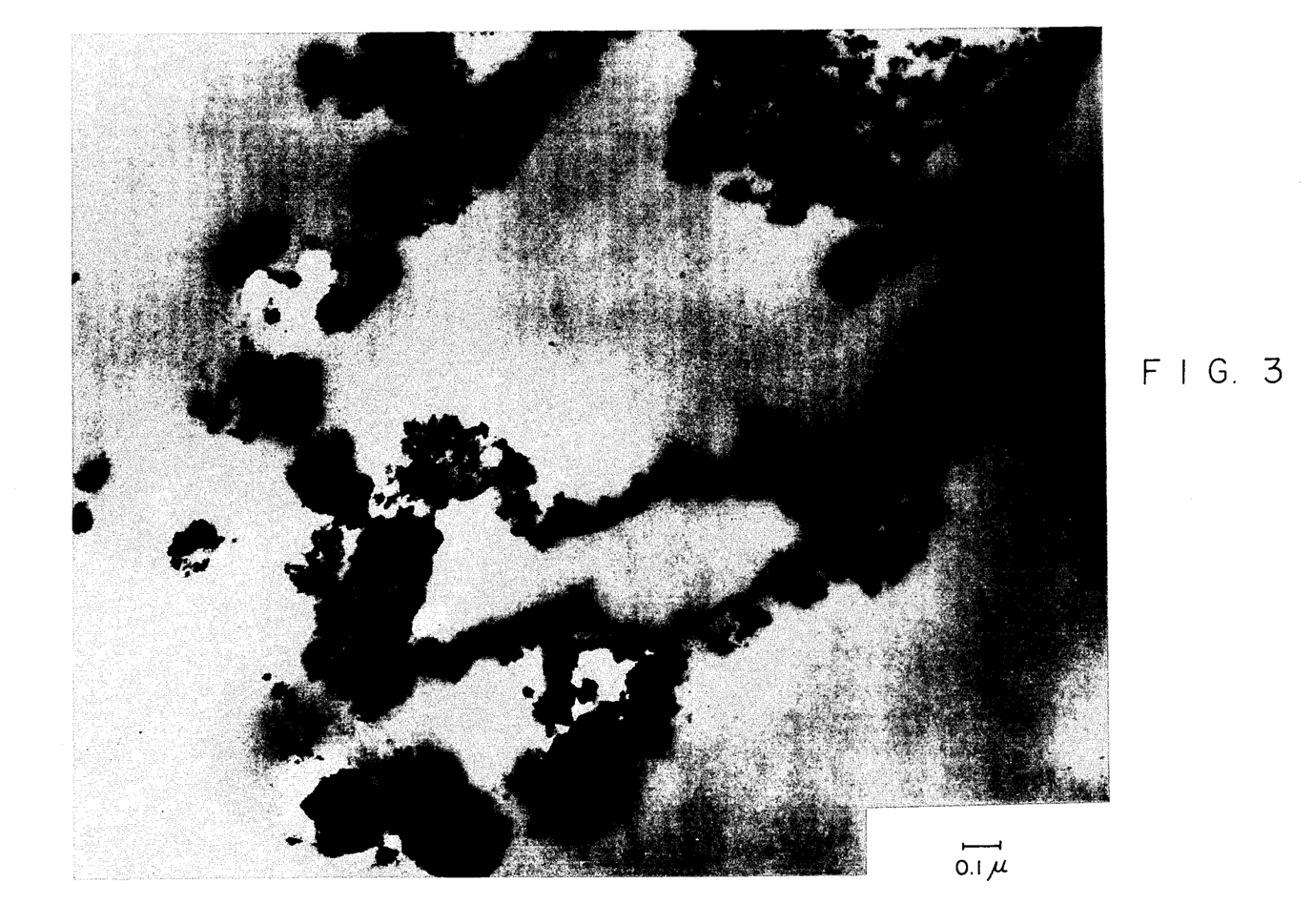
FIG. 3 is an electron microscope photograph at 84,000 magnification of rhodium of the present invention prepared by the same method used in FIG. 2.
Figure 4:
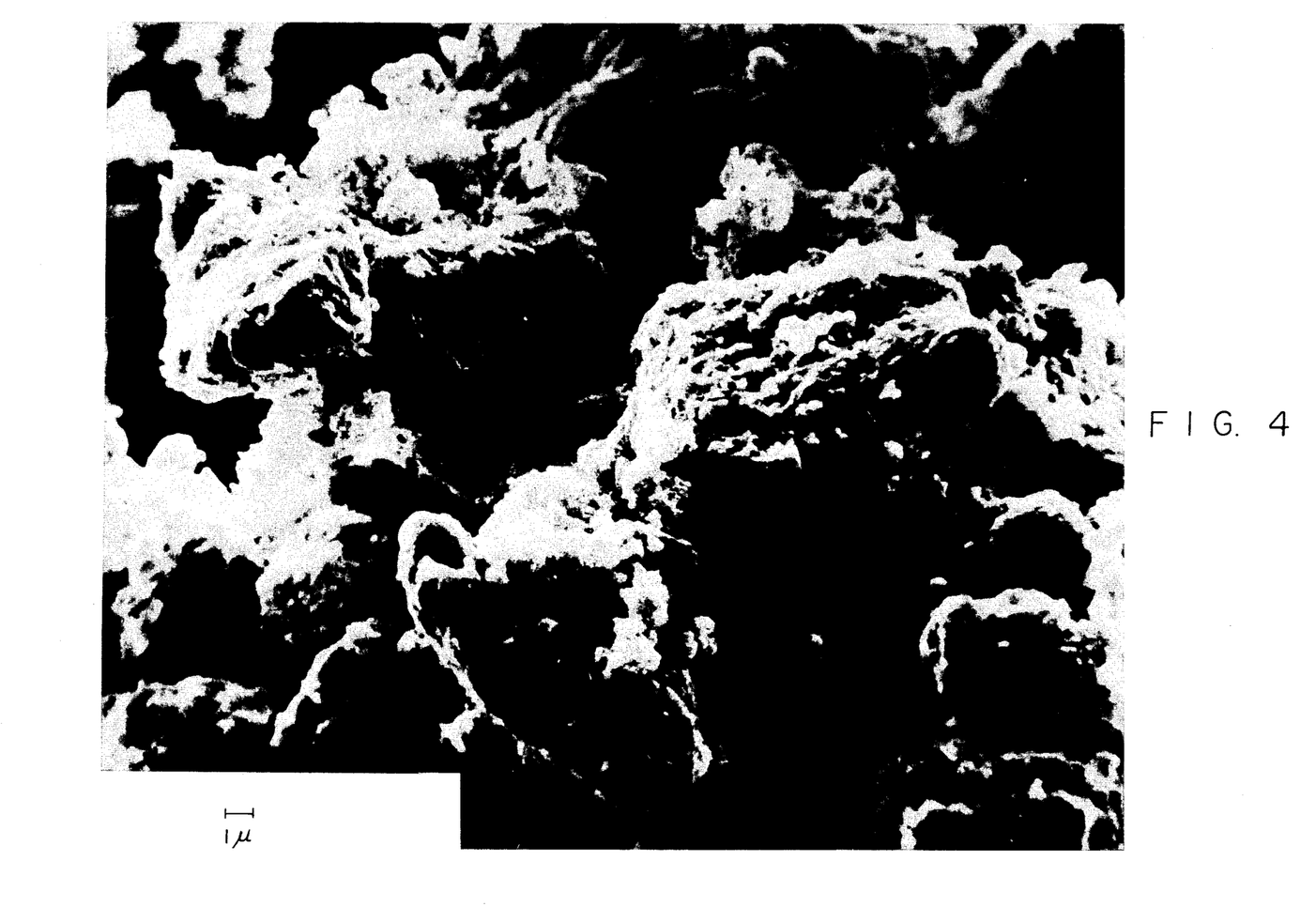
FIG. 4 is an electron microscope photograph at 6,000 magnification of commercially available metallic rhodium.
Figure 5:
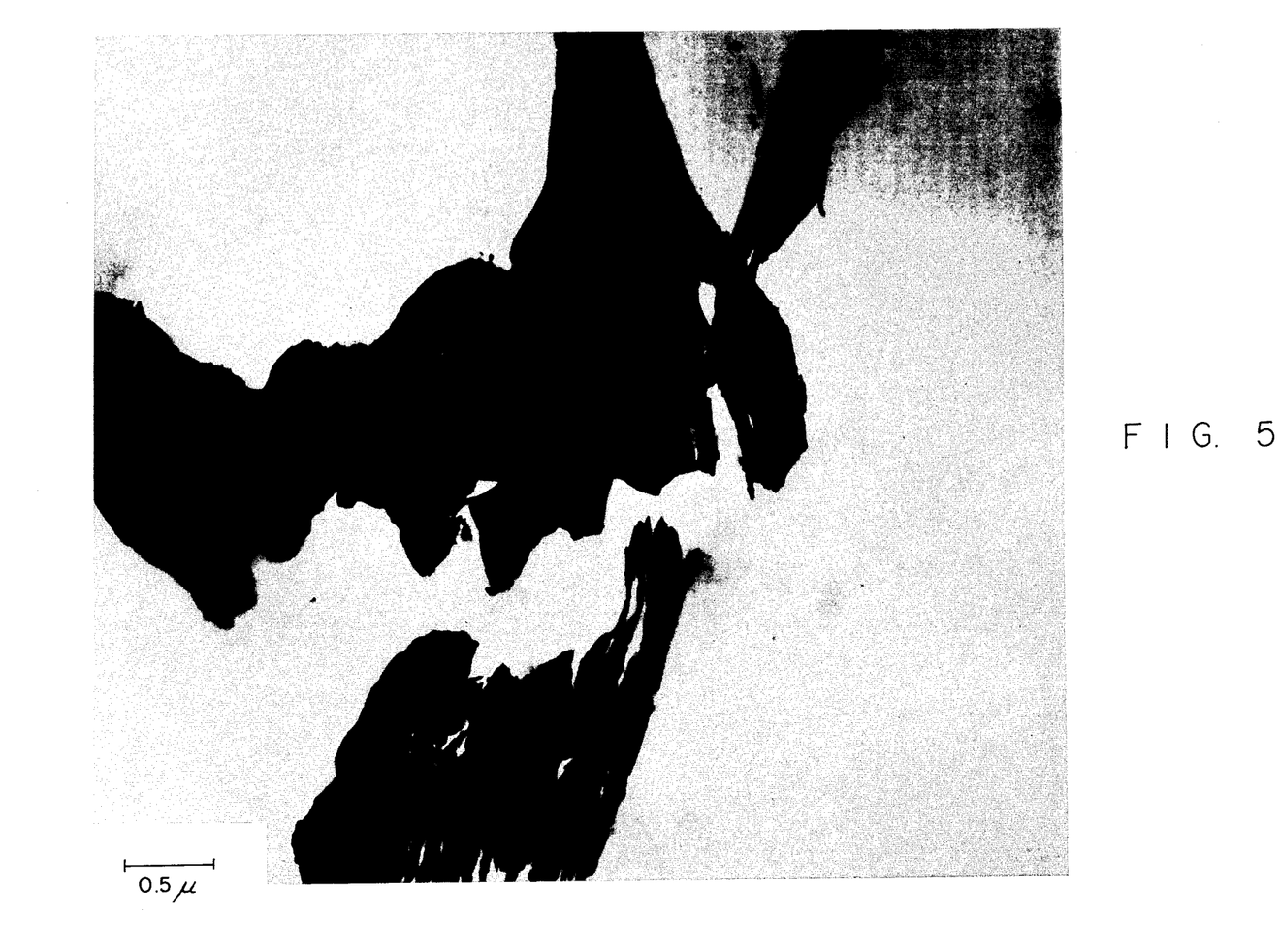
FIG. 5 is an electron microscope photograph at 40,000 magnification of commercially available metallic rhodium prepared in the same manner as the rhodium in FIG. 2.

The surface area of the rhodium of FIG. 3 was determined to be about 5.4 square meters per gram. The surface area of commercially available metallic rhodium was calculated, based on the smallest particle size commercially available namely 325 mesh particles, to be $1 \times 10^{-5}$ square meters per gram. Thus, the surface area of the rhodium of this invention is at least about five orders of magnitude greater than commercially available metallic rhodium. The rhodium of the present invention is readily filterable due to the porous agglomerate form in which it is prepared. Unagglomerated nonporous forms of rhodium particles of the size indicated would be very difficult to filter.

The hydrothermal treatment of still heels from the catalytic hydroformylation of unsaturated hydrocarbons, preferably cyclic acetals, result in the recovery of at least 90% of the rhodium present in the still heels according to the process of the present invention. Depending on the conditions, recovery of rhodium can be as much as 95% or more of the rhodium present in the still heels.

Under the preferred conditions as much as 95% or more of the rhodium present in still heels can be recovered. The preferred conditions are 160° C for two hours, a 0.3:1 weight ratio of water to still heels, an air atmosphere and a beginning and final pH within the range of 3 to 7.

The still heels of the process of the present invention can conveniently be illustrated by reference to a specific hydroformylation reaction. Thus, 2-vinyl-5-methyl 1,3-dioxane is hydroformylated in the presence of carbon monoxide, hydrogen, zero valent rhodium and trimethyl phosphite and the reaction product thereof is distilled to remove trimethyl phosphite and the products indicated in the equations below.

The residue from the distillation consists of rhodium and high boilers (HB). Portions of said residue when treated according to the present invention have yielded 99.5% rhodium based on the initial rhodium concentration and the metallic rhodium that resulted possessed increased surface area over commercially available metallic rhodium and said rhodium was in the form of small, porous, hollow agglomerates of particles.

Metallic rhodium of the present invention is easily solubilized or made into a homogenous solution for use as a catalyst in hydroformylation reactions. This was accomplished, e.g., by mixing said metallic rhodium with 114 moles of trimethyl phosphite per gram of rhodium at 150° C for 2 hours under a H₂/CO pressure of 4,000 psig said H₂/CO being present at a molar ratio of 1:1, thus converting greater than 90% of the rhodium prepared by the process of the present invention into soluble catalyst containing Rh, carbonyl, ligand and hydrogen and is probably a rhodium hydrido carbonyl ligand type of compound. The high conversion to soluble catalyst is believed to be due to the high surface area of the rhodium of this invention.

A sample of high surface area metallic rhodium of the present invention prepared from still heels was subjected to Electron Spectroscopy for Chemical Analysis (ESCA). The surfaces of the agglomerates and of the particles were found to be essentially metallic rhodium. The ESCA technique probed only approximately the top 30 A of the sample's surface and it was this analysis that indicated that the rhodium of the present invention was metallic. X-ray fluoresence also has confirmed the presence of metallic rhodium.

The process of the present invention is conducted under an atmosphere that can be air, oxygen or nitrogen. Generally highest recovery results are obtained in oxygen while in air the recovery is better than in nitrogen. For example, in an oxygen atmosphere the process of the present invention produced 99.5% by weight of rhodium based on the starting rhodium level.

In the following examples where the present invention is further illustrated all percentages and parts are by weight unless otherwise indicated.

EXAMPLE 1

To fifteen grams of hydroformylation still heels containing 25.3 mg Rh, from the hydroformylation reaction of 2-vinyl-5-methyl-1,3-dioxane in the presence of trimethyl phosphite ligand, was added 2.5 ml of water and the mixture heated with stirring and in the presence of air for 45 minutes at 160° C in a closed stainless steel reactor. The cooled reaction mixture was diluted with methanol to reduce the viscosity and filtered by suction through a Reeve Angle glass fiber filter disc (Grade 984H). A solid product weighing 32.1 mg containing rhodium metal powder was obtained. The filtrate was analyzed by atomic absorption and found to contain 0.36 mg rhodium. Rhodium recovery was 98.6% based on the rhodium content of the still heels and of the final filtrate.

EXAMPLES 2-5

The same procedure and equipment was used in the following examples as was employed in Example 1.

|  | Examples | | | |
|---|---|---|---|---|
|  | 2 | 3 | 4 | 5 |
| Still heels (g) | 15.0 | 15.0 | 15.0 | 15.0 |
| Water (ml) | 2.5 | 2.5 | 3.5 | 2.0 |
| Atmosphere | $N_2$ | air | air | $N_2$ |
| Temperature (° C) | 160 | 160 | 160 | 150 |
| Time (min.) | 45 | 60 | 90 | 30 |
| Rh recovery (%) | 98.8 | 99.0 | 99.5 | 98.6 |
| Weight ratio of water or water/alcohol to still heels | 0.12:1 | 0.17:1 | 0.23:1 | 0.13:1 |

EXAMPLES 6-13

The same procedure and equipment was used in the following examples as employed in Example 1. An aqueous alcohol (n-butanol/n-propanol/$H_2O$ = 1/1/1.5 by volume) was used to (a) provide the required water and (b) lower the viscosity of the reaction mixture. The addition of a small amount of sodium hydroxide in the form of a 2 normal aqueous solution to the reaction mixture before heating was necessary to adjust the pH of the mixture treated.

|  | Examples | | | | | | | |
|---|---|---|---|---|---|---|---|---|
|  | 6 | 7 | 8 | 9 | 10 | 11 | 12 | 13 |
| Still heels (g) | 15.0 | 15.0 | 15.0 | 15.0 | 15.0 | 15.0 | 15.0 | 15.0 |
| Aqueous alcohol (ml) | 7.0 | 7.0 | 7.0 | 7.0 | 7.0 | 15.0 | 0 | 7.0 |
| NaOH (meq.) | 0 | 0.2 | 0.8 | 1.6 | 0.2 | 0.2 | 0.2 | 0.2 |
| Atmosphere | $N_2$ | $N_2$ | $N_2$ | $N_2$ | air | $O_2$ | $O_2$ | $O_2$ |
| Temperature (° C) | 160 | 160 | 160 | 160 | 160 | 160 | 160 | 140 |
| Time (min.) | 60 | 60 | 60 | 60 | 90 | 90 | 90 | 90 |
| Rh recovery (%) | 95.5 | 98.5 | 97.5 | 97.4 | 99.1 | 99.2 | 61.9 | 98.1 |
| Weight ratio of aqueous alcohol to still heels | .41:1 | .41:1 | .41:1 | .41:1 | .41:1 | .87:1 | & — | .41:1 |

EXAMPLES 14-16

The same procedure and equipment was used in the following examples as employed in Example 1. The same aqueous alcohol was used as described for Examples 6-13.

|  | Examples | | |
|---|---|---|---|
|  | 14 | 15 | 16 |
| Still heels (g) | 7.0 | 7.0 | 7.0 |
| Aqueous alcohol (ml) | 1.75 | 1.75 | 1.75 |
| Atmosphere | air | air | air |
| Temperature (° C) | 150 | 130 | 115 |
| Time (min.) | 20 | 30 | 30 |
| Rh recovery (%) | 97.6 | 92.3 | 84.5 |
| Weight ratio of aqueous alcohol to still heel | .22:1 | .22:1 | .22:1 |

The process of the present invention also may be described as a process for the recovery of rhodium metal catalyst from the reaction product of hydroformylation of cyclic acetals. In the hydroformylation of cyclic acetals, e.g., 2-vinyl-5-methyl 1,3-dioxane in the presence of carbon monoxide, hydrogen and a complex rhodium ligand catalyst wherein the ligand is as described herein to give cyclic acetal aldehydes, it is necessary to recover the catalyst from the acetal aldehyde reaction product for recycling back to the hydroformylation for economic reasons. However, hydroformylation unavoidably involves the formation of high boiling byproducts, e.g., high boiling aldol condensation products and these are present in still heels with the catalyst. The continuous recycling of catalyst causes the excessive accumulation of high boiling products in the hydroformylation reaction. The present process permits the easy recovery of rhodium from the catalyst and high boilers in a form that is readily convertable to active catalyst.

The rhodium of the present invention is useful as a catalyst in the hydroformylation of olefins.

While the invention has been described in considerable detail in the foregoing, it is to be understood that such detail is solely for the purpose of illustration and

What is claimed is:

1. A process for preparing a high surface area, metallic rhodium in the form of small, hollow, porous agglomerates of rhodium particles from still heels from the hydroformylation of an unsaturated hydrocarbon in the presence of a rhodium trialkyl phosphite ligand complex catalyst whereby 90% or more of the rhodium present in the still heels is converted to said rhodium form, said process comprising
    a. adjusting the pH of the still heels from about 3 to about 8 with a base selected from an alkali metal hydroxide and an alkaline earth metal hydroxide;
    b. heating the solution from (a) for from about 15 minutes to about 120 minutes at about 115° to about 175° C in the presence of water, the ratio of water to still heel being from about 0.1:1 to 1:1; and
    c. recovery the rhodium in the form of hollow spheres of agglomerated particles.
2. The process of claim 1 wherein the water is present with an alcohol.
3. The process of claim 1 wherein the water is present in a mixture with an organic liquid.
4. The process of claim 1 wherein the pH of the still heels is adjusted with sodium hydroxide.
5. The process of claim 1 wherein the unsaturated hydrocarbon is an olefinic cyclic acetal.
6. High surface area metallic rhodium in the form of small, hollow, porous agglomerates of particles having a surface area of about 1 square meter per gram or more.
7. The rhodium of claim 6 wherein the particles range in size from about 0.01 to 0.5 micron in diameter.
8. High surface area metallic rhodium in the form of small, hollow, porous agglomerates of particles prepared by the process comprising
    a. adjusting the pH of the still heels from about 3 to about 8 with a base selected from an alkali metal hydroxide and an alkaline earth metal hydroxide;
    b. heating the solution from (a) for from about 15 minutes to about 120 minutes at about 115° to about 175° C in the presence of water, the ratio of water to still heel being from about 0.1:1 to 1:1; and
    c. recovering the rhodium in the form of hollow spheres of agglomerated particles.
9. The product of claim 8 wherein the process is conducted in the presence of water with an alcohol.
10. The product of claim 8 wherein the process is is conducted in the presence of water with an organic liquid.
11. The product of claim 8 wherein the process of adjusting the pH is accomplished with sodium hydroxide.

* * * * *